(12) United States Patent
Woo et al.

(10) Patent No.: US 6,504,018 B1
(45) Date of Patent: Jan. 7, 2003

(54) PROCESS FOR PREPARING PALE-COLORED AND TRANSPARENT ALKYL GLYCOSIDES

(75) Inventors: Tae-Hee Woo, Taejeon; Dong-Hyuh Cho, Seoul; Kwang-Ho Park, Taejeon, all of (KR)

(73) Assignee: L G Chemical Ltd., Seoul (KR)

( * ) Notice: Subject to any disclaimer, the term of this patent is extended or adjusted under 35 U.S.C. 154(b) by 0 days.

(21) Appl. No.: 09/554,639

(22) PCT Filed: Nov. 20, 1998

(86) PCT No.: PCT/KR98/00370

§ 371 (c)(1),
(2), (4) Date: May 17, 2000

(87) PCT Pub. No.: WO99/26957

PCT Pub. Date: Jun. 3, 1999

(30) Foreign Application Priority Data

| Nov. 22, 1997 | (KR) | 97-62224 |
| Nov. 22, 1997 | (KR) | 97-62225 |
| Nov. 22, 1997 | (KR) | 97-62236 |
| Jun. 3, 1998 | (KR) | 97-20631 |

(51) Int. Cl.$^7$ .......... C07G 11/00; C07G 3/00; C07G 17/00; C07H 15/04; C07H 1/06

(52) U.S. Cl. .......... 536/18.6; 536/4.1; 536/120; 536/124; 536/127

(58) Field of Search .......... 536/4.1, 18.6, 536/120, 124, 127

(56) References Cited

U.S. PATENT DOCUMENTS 5,554,740 A * 9/1996 McCurry, Jr. et al. ....... 536/4.1

* cited by examiner

Primary Examiner—Jezia Riley
(74) Attorney, Agent, or Firm—Nixon Peabody LLP

(57) ABSTRACT

A process for preparing pale-colored and transparent alkyl glycosides by reacting glucose and high fatty alcohol in presence of an acid catalyst is disclosed. The process comprises the steps of admixing, reacting, neutralizing, distilling, diluting and bleaching. In the above process, the reaction step is controlled by a product color and an amount of unreacted glucose, the neutralizing step is controlled by alkali metal oxdie powders having a specific surface area of more than 30 m$^2$/g and the product color, the distilling step is controlled an unreacted residual fatty alcohol, and the diluting step is controlled by refined ion water and sealed vessel without oxygen. Further, the process provides a method of recycling collected fatty alcohol without being refined.

34 Claims, No Drawings

PROCESS FOR PREPARING PALE-COLORED AND TRANSPARENT ALKYL GLYCOSIDES

BACKGROUND OF THE INVENTION (a) Field of the Invention

The present invention relates to a process for preparing alkyl glycosides, and more particularly to a process for preparing pale-colored and transparent alkyl glycosides.

(b) Description of the Related Art

Alkyl glycosides are non-ionic surfactants made from natural materials, which provide detergency, foaming, emulsifying, and wetting properties comparable to those of other non-ionic surfactants. Alkyl glycosides have an advantage of reducing water pollution as applied to detergents since they have a superior biodegradability, and also because of their hypo-allergenic property they are suitable for decreasing allergic reactions of skin commonly associated with the detergents.

Conventionally, alkyl glycosides are prepared by a method of reacting carbohydrates with low fatty alcohol such as butyl alcohol in presence of an acid catalyst such as sulfuric acid or hydrochloric acid, and then reacting carbohydrates with high fatty alcohol as disclosed in German Patent Application No. 3 723 826 A1; German Patent Application No. 3 827 534 A1; German Patent Application No. 3 842 541 A1; EPO Publication No. 0 306 650 A1; EPO Publication No. 0 306 651 A1 and EPO Publication No. 0 306 652 A1. Because the method utilizes two reacting steps having a long reaction time, the process becomes complex. Additionally, there is a drawback in that the high fatty alcohol and low fatty alcohol must be stored separately, further complicating the method.

To solve the above problems, EPO Publication No. 0 387 913 A1 and EPO Publication No. 0 388 857 A1 describe a process of reacting carbohydrate such as glucose with high fatty alcohol in presence of an acid catalyst. This method has a problem in that removing an excess of unreacted high fatty alcohol cause brown color to develop. In the neutralization step, an alkaline substance is added to remove remaining acids from the reaction, in order to prevent the alkyl glycosides from reversibly decomposing into glucose and alcohol at a high temperature. However, in the above neutralization step, an exact neutralization point is difficult to obtain, and consequently adding an alkaline substance in excess is not an uncommon problem. An excess of alkaline substance in the above step cause brown color to develop, also attributed by the presence of carbohydrates, oxygen, high temperature, alkali, proteins, metal ions, minerals or vitamins.

To solve the above problem, U.S. Pat. No. 4,950,743; EPO Publication No. 0 362 671 A1; EPO Publication No. 0 389 753 A1; German Patent Application No. 3 940 827 A1 and German Patent Application No. 4 019 175 A1 describe a method of bleaching alkyl glycosides with peroxide such as hydrogen peroxide or ozone ($O_3$), and stabilizing with sodium borohydride ($NaBH_4$). This method has problems in that it provides an unsatisfied degree of color (closest to transparency), and color reversion may occur during storage of surfactants.

PCT Publication No. WO 94/02494; PCT Publication No. 94/24139 and PCT Publication No. 95/23169 describe methods utilizing a neutralizing agent having a weak alkaline substance such as a mixture of sodium hydroxide and magnesium oxide in order to decrease the color reversion. Again, these methods fall short of solving the above problem of removing brown coloration while obtaining a satisfactory degree of color closest to transparency.

Additionally, in the conventional methods, there is a further drawback in that the removed fatty alcohol, still having brown coloration, cannot be utilized again until it is refined in a distillation process and have its color removed. This additional step complicates and adds cost to the manufacturing process.

SUMMARY OF THE INVENTION

It is an object of the present invention to provide a process for preparing pale-colored and transparent alkyl glycosides.

Another object is to provide a process of collecting excess fatty alcohol without a refining step.

To achieve the above objects the present invention provides a process for preparing pale-colored and transparent alkyl glycosides by reacting a glucose with a high fatty alcohol in presence of an acid catalyst, comprising the steps of admixing, reacting, neutralizing, distilling, diluting and bleaching. In the above process, the reacting step is controlled by a product's color and an amount of unreacted glucose; the neutralizing step is controlled by alkali metal oxide powders and the product's color; the distilling step is controlled by an unreacted fatty alcohol; and the diluting step is controlled by refined ion water and sealed vessel without oxygen.

Additional objects, advantages and novel features of the invention will be set forth in part in the description which follows, and in part will become apparent to those skilled in the art upon examination of the following or may be learned by practice of the invention. The object and advantage of the invention may be realized and attained by means of the instrumentality and combinations particular pointed out in the appended claims.

DETAILED DESCRIPTION OF THE INVENTION

The preferred processes according to the present invention will now be described in detail.

A first preferred process for preparing pale-colored and transparent alkyl glycosides according to the present invention comprises the steps of:

1) admixing a carbohydrate such as glucose with high fatty alcohol having 8 to 22 carbon atoms;

2) reacting the mixture in presence of an acid catalyst such as p-toluene sulfonic acid (p-TSA) at a high temperature under a high vacuum condition until the reaction product's color is between ochre and wormwood and the amount of unreacted glucose is less than 3% of the reactants' weight;

3) neutralizing the reaction product having water content of less than 1000 ppm by adding neutralizing agent such as alkali metal oxide powders that have a specific surface area of more than 30 $m^2/g$, and stirring until the reaction product's color is yellow and the reaction product pH is 7.0~8.0;

4) distilling the neutralized reaction product to remove the unreacted residual fatty alcohol at a high temperature under a high vacuum condition until the amount of the unreacted fatty alcohol is less than 2% of the distilled reaction product's weight;

5) diluting the distilled reaction product by adding refined ion water having pH of 2.0~6.0, in a vessel sealed and charged with nitrogen gas; then 6) bleaching the diluted reaction product with a small amount of bleaching agent such as hydrogen peroxide.

In the above steps, it is preferable that the amount of fatty alcohol in step 1) is 3~5 mole per mole of glucose; the amount of acid catalyst in step 2) is 0.002~0.007 mole per mole of glucose; the reaction temperature is 110~125° C.; the reaction pressure is 16~20 torr; and the reaction time is 80~200 minutes.

The preferred alkali metal oxide of the neutralizing agent in step 3) is magnesium oxide, aluminum oxide, calcium oxide, zinc oxide or their mixture and the amount used is between 0.5 mole and 1.0 mole based on the acid catalyst used. The stirring temperature is between 85° C. and 105° C., and the stirring time is between 20 minutes and 40 minutes.

It is also preferable that the distillation instrument in step 4) is a thin film evaporator, and that the color of the diluted reaction product in step 5) is yellow having between 4 and 11 Gardner number.

The preferred vessel in step 5) have an outlet operated automatically by a level sensor or a pressure sensor and the dilute concentration is between 40% and 60%. Also a residue of the bleaching agent in step 6) may be decreased from the reaction product by a heat exchanger.

A second preferred process according to the present invention will now be described below.

1) reacting glucose and high fatty alcohol of having 8 to 22 carbon atoms, in presence of an acid catalyst until the amount of unreacted glucose in reaction product is less than 3% of the distilled reactant product' weight;

2) neutralizing the reaction product by adding magnesium oxide powders having a specific surface area of more than 50 m$^2$/g, preferably more than 80 m$^2$/g, at 85~105° C. temperature for 20~40 minutes;

3) distilling the neutralized reaction product until the amount of the unreacted residual fatty alcohol is less than 2% of the reactants' weight;

4) diluting the distilled reaction product; then 5) bleaching the diluted reaction product with hydrogen peroxide.

In the above process, it is preferable that the acid catalyst is para-toluene sulfonic acid in the reacting step and that the amount of magnesium oxide used is between 0.5 mole and 1.0 mole, based on the acid catalyst used.

A third preferred process according to the present invention will be described below.

1) reacting glucose and high fatty alcohol of having 8 to 22 carbon atoms in presence of an acid catalyst until the amount of unreacted glucose in reaction product is less than 3% of the reactants' weight;

2) neutralizing the reaction product having water content of less than 1000 ppm, preferably less than 500 ppm, by adding alkali metal oxide powders such as magnesium oxide, aluminum oxide, calcium oxide, zinc oxide or their mixture having a specific surface area of more than 30 m$^2$/g, preferably more than 50 m$^2$/g.

In the above process, it is preferable that the amount of alkali metal oxide used is between 0.5 mole and 1.0 mole, based on the acid catalyst used, and that the neutralization is carried out by stirring for 20~60 minutes at 85~105° C. temperature until the pH of the neutralized reaction product is between 7.0 and 8.0.

A fourth preferred process according to the present invention will be described below.

1) reacting glucose and high fatty alcohol in presence of an acid catalyst;

2) neutralizing the reaction product by adding neutralizing agent until the reaction product' pH is 7.0~8.0;

3) distilling the neutralized reaction product; then 4) diluting the distilled reaction product by adding refined ion water having pH 2.0~6.0, preferably pH of 3.0~5.0, in a vessel sealed and charged with nitrogen gas.

In the above process, it is preferable that the vessel has an outlet operated automatically by a level sensor or a pressure sensor.

A fifth preferred process according to the present invention will be described below.

1) admixing a carbohydrate such as glucose with high fatty alcohol having 8 to 22 carbon atoms;

2) reacting the mixture in presence of an acid catalyst until the reaction product's color is between ochre and wormwood and the amount of unreacted glucose is less than 3% of the reactants' weight;

3) neutralizing the reaction product by adding magnesium oxide powders, and stirring until the reaction product's color is yellow;

4) distilling the neutralized reaction product until the amount of the unreacted residual fatty alcohol is less than 2% of the distilled reaction product's weight;

5) diluting the distilled reaction product; then 6) bleaching the diluted reaction product with hydrogen peroxide.

In the above steps, it is preferable that the neutralization is carried out by stirring for 20~60 minutes at 85~105° C.

In accordance with the present invention, factors that affect color quality and cleaning effect of detergents are described below.

The first factor is a length of carbon chain that a fatty alcohol contains. Generally, alkyl glycosides made from a fatty alcohol containing less than 10 carbon atoms have a superior degree of color, and they are very hydrophilic that they may be soluble in water. However, alkyl glycosides made from a fatty alcohol containing more than 12 carbon atoms have an inferior degree of color, and they are very hydrophobic that they are suitable as emulsifying agent or wetting agent. Accordingly, a mixture of both the high and low number carbon chain fatty alcohol is employed as raw materials for a detergent having a superior degree of color and a cleaning effect.

The second factor is a mole ratio of fatty alcohol to glucose. For example, if the mole ratio of fatty alcohol and glucose (A/G) is over 5, the product may have a good degree of color that may be found at the end point of reaction without difficulty. However, the product has an inferior cleaning effect because of it's a low degree of oligomerization. On the other hand, if the mole ratio is below 2 or 3, the product may have an inferior degree of color. Hence, it is preferable that the reaction mole ratio of fatty alcohol to glucose is between 3 to 5 to obtain alkyl glycosides having a superior degree of color and cleaning effect.

The third factor is an oxygenation of reaction product produced at a temperature above 130° C. while removing excess fatty alcohol. The oxygenation provides final product having an inferior degree of color.

The fourth factor is a neutralizing condition such as pH. In the neutralizing step it is difficult to control pH with a neutralizing agent. If the neutralization is not sufficient, the reaction may be reversed and alkyl glycosides may decompose to glucose and alcohol, and the isolated glucose becomes a caramel. If the neutralization is excessive, the product may become an alkaline substance and brown coloration may develop. Hence, it is preferable that pH is maintained in a range of 7.0 to 8.0. The temperature and the time required in the neutralizing step also influence pH and color quality.

Accordingly, it is preferable that in the admixing step the amount of fatty alcohol is 3~5 mole per mole of glucose; that in the reacting step the amount of acid catalyst is 0.002~0.007 mole per mole of glucose; the reaction temperature is 110~125° C.; the reaction vacuum pressure is 16~20 torr; the reaction time is 80~200 minutes; and the amount of unreacted glucose is below 3% of the reactants' weight.

In the neutralizing step of the present invention, a neutralizing agent employed is alkali metal oxide powders such as magnesium oxide, aluminum oxide, calcium oxide, zinc oxide in an amount between 0.5 mole and 1.0 mole, based on the amount of acid catalyst used, on a molar basis. The stirring temperature range is from 85° C. to 105° C.; stirring time is between 20 minute to 40 minute; neutralizing end point range is from pH of 7.0 to 8.0.

In distilling step of the present invention, the reaction product distilled by heat should have an unreacted fatty alcohol below 2% of the distilled reaction product's weight. And it is desirable to cool the distilled reaction product quickly until the product temperature reaches below 130° C. for obtaining a superior degree of color. And the collection of the distilled excess fatty alcohol can be recycled without the refining step.

In the diluting step of the present invention, the controlled reaction product color is yellow having Gardner number range of from 4 to 11.

In the bleaching step of the present invention, after removing the residue of the bleaching agent by a heat exchanger, the product obtained is pale and transparent color.

The following examples illustrate the advantages of the present invention.

EXAMPLE 1

To a vessel with an over head stirrer and addition funnel, was added a mixture of fatty alcohol comprised of 22 parts of $C_8$, 17 parts of $C_{10}$, 47 parts of $C_{12}$ and 14 parts of $C_{14}$ by weight. Stirring was started and glucose was admixed. The amount of admixture was 100 kg and a weight ratio of fatty alcohol to glucose was 3.5.

155 grams of p-toluene sulfonic acid catalyst was added under vacuum.

The pressure was reduced to 20 torr and the mixture was heated and reacted at a temperature range of from 116° C. to 120° C. for 100 minutes.

To this mixture was then added 22 grams of magnesium oxide powders having 100 m²/g of specific surface area and 1% moisture content. The mixture was stirred for 30 minutes at a pot temperature of 95° C.

The neutralized mixture was then distilled under a vacuum pressure of below 0.5 torr at a heat temperature of below 200° C. At this point in the process, the distilled mixture contained an alcohol residue having less than 2% of the distilled reaction product's weight.

The distilled mixture was then diluted with 34 kg of refined ion water equal to the amount of distilled mixture.

The diluted solution was found to have water content of 50%, and a Gardner color number of 5.4.

To the diluted mixture was added 0.9 kg of 30% aqueous solution of sodium hydroxide and was dissolved for 10 minute at a pot temperature of 50° C. And then, 1.7 kg of 28% aqueous solution of hydrogen peroxide was added and stirred for 2 hours at 85° C.

The bleached solution was found to have pale-colored and transparent alkyl glycosides having water content of 49.6%, transmittance of 95% and APHA of 30 by an examination with naked eye and instrumental analysis using a tintometer (Lovibond's PFX 190) and transmittance analyser (Milton Roy's spectronic 20 D). The collected alcohol had APHA of 0.

EXAMPLE 2

Alkyl glycosides was obtained by the process steps of Example 1, except 25 grams of magnesium oxide powders having 80 m²/g of specific surface area and 1% of moisture content was utilized.

The diluted solution was found to have water content of 50%, and a Gardner color number of 6.0.

The bleached solution was found to have pale-colored and transparent alkyl glycosides having water content of 49.5%, transmittance of 93%, and APHA of 48. The collected alcohol had APHA of 10.

Comparative Example A

For comparison purposes, alkyl glycosides was obtained by the process steps of Example 1, except 35 grams of magnesium oxide powders having 30 m²/g of specific surface area and 1% of moisture content was utilized.

The diluted solution was found to have water content of 50%, and a Gardner color number of 8.7.

The bleached solution was found to have semi-transparent alkyl glycosides having water content of 48.6%, transmittance of 60%, and APHA of 80. The collected alcohol had APHA of 20.

Comparative Example B

Alkyl glycosides was obtained by the process steps of Example 1, except 62 grams of magnesium oxide powders having 10 m²/g of specific surface area and 1% of moisture content was utilized.

The diluted solution was found to have water content of 50%, and a Gardner color number of 9.5.

The bleached solution was found to have semi-transparent alkyl glycosides having water content of 49.5%, transmittance of 45%, and APHA of 190. The collected alcohol had APHA of 30.

Comparative Example C

Alkyl glycosides was obtained by the process steps of Example 1, except 11 grams of magnesium oxide powders having 65 m²/g of specific surface area and 1% of moisture content and 104 g of 30% aqueous solution of sodium hydroxide were utilized.

The diluted solution was found to have water content of 50%, and a Gardner color number of 15.5.

The bleached solution was found to have opaque alkyl glycosides having water content of 49.5%, transmittance of 25%, and APHA of 320. The collected alcohol had APHA of 80.

EXAMPLE 3

To a vessel with an over head stirrer and addition funnel, was added a mixture of fatty alcohol comprised of 22 parts of $C_8$, 17 parts of $C_{10}$, 47 parts of $C_{12}$ and 14 parts of $C_{14}$ by weight. Stirring was started and glucose was admixed. The amount of admixture was 100 kg and a weight ratio of fatty alcohol to glucose was 3.5.

155 grams of p-toluene sulfonic acid catalyst was added under vacuum.

The pressure was reduced to 20 torr and the mixture was heated and reacted at a temperature range of from 116° C. to 120° C. for 100 minutes.

To this mixture was then added 35 grams of magnesium oxide powders having 30 m$^2$/g of specific surface area and 1% of moisture content. The mixture was stirred for 30 minutes at a pot temperature of 95° C.

The neutralized mixture was then distilled under a vacuum pressure of below 0.5 torr at a heat temperature of below 200° C. At this point in the process, the distilled mixture contained an alcohol residue having less than 2% of the distilled reaction product's weight.

The distilled mixture was then diluted with 34 kg of refined ion water of pH 4.5 equal to the amount of distilled mixture. The diluting step was carried out in the sealed vessel which have an outlet operated automatically by a level sensor or a pressure sensor, and nitrogen gas was poured into the vessel in the beginning of dilution in order to prevent the mixture from being exposed to oxygen.

The diluted solution was found to have water content of 50%, and a Gardner color number of 7.2.

To the diluted mixture was added 0.9 kg of 30% aqueous solution of sodium hydroxide and was dissolved for 10 minute at a pot temperature of to about 50° C. And then, 1.7 kg of 28% aqueous solution of hydrogen peroxide was added and stirred for 2 hours at 85° C.

The bleached solution was found to have pale-colored and transparent alkyl glycosides having water content of 49.6%, transmittance of 84%, and APHA of 60 by an examination with naked eye and instrumental analysis using a tintometer (Lovibond's PFX 190) and transmittace analyser (Milton Roy's spectronic 20 D). The collected alcohol had APHA of 20.

Comparative Example D

For comparison purposes, alkyl glycosides was obtained by the process steps of Example 1, except 35 grams of magnesium oxide powders having 30 m$^2$/g of specific surface area and 1% of moisture content was utilized. And the neutralization was carried out for 90 minutes instead of 30 minutes, and the neutralized solution color was becoming light yellow or bright yellow.

The diluted solution was found to have water content of 50%, and a Gardner color number of 9.2.

The bleached solution was found to have semi-transparent alkyl glycosides having transmittance of 54% and APHA of 100. The collected alcohol was found to have APHA of 35.

EXAMPLE 4

Alkyl glycosides was obtained by the process steps of Example 1, except reaction time proceeded until the reaction solution color was between ochre and wormwood, and 35 grams of magnesium oxide powders having 30 m$^2$/g of specific surface area and 1% of moisture content was utilized. And the neutralization was carried out for 30 minutes, and the neutralized solution color was becoming yellow.

The diluted solution was found to have water content of 50%, and a Gardner color number of 7.8.

The bleached solution was found to have transparent alkyl glycosides having transmittance of 75% and APHA of 70. The collected alcohol had APHA of 16.

Comparative Example E

For comparison purposes, alkyl glycosides was obtained by the process steps of Example 1, except a reaction product having moisture content of 1.25% and 35 grams of magnesium oxide powders having 30 m$^2$/g of specific surface area and 1% of moisture content were utilized. And the neutralization condition was carried out in atmospheric pressure.

The neutralized reaction product was decomposed to alcohol and glucose, and became a caramel owing to oligomerization of glucose in the step of distillation.

EXAMPLE 5

Alkyl glycosides was obtained by the process steps of Comparative Example E, but a vacuum of 150 torr was used in the neutralizing step.

The neutralized reaction product was not found to be a caramel.

The diluted solution was found to have water content of 50%, Gardner color number of 8.2.

The bleached solution was found to have transparent alkyl glycosides having transmittance of 70%, and APHA of 74. The collected alcohol had APHA of 18.

EXAMPLE 6

To a vessel with an over head stirrer and addition funnel, was added a mixture of fatty alcohol comprised of 22 parts of $C_8$, 17 parts of $C_{10}$, 47 is parts of $C_{12}$ and 14 parts of $C_{14}$ by weight. Stirring was started and glucose was admixed. The amount of admixture was 100 kg and a weight ratio of fatty alcohol to glucose was 3.5.

155 grams of p-toluene sulfonic acid catalyst was added under vacuum.

The pressure was reduced to 20 torr and the mixture was heated and reacted at a temperature of from 116° C. to 120° C. for 100 minutes until the reaction product's color reached between ochre and wormwood.

To this mixture having water content of less than 1000 ppm was then added 22 grams of magnesium oxide powders having 100 m$^2$/g of specific surface area and 1% of moisture content. The mixture was stirred for 30 minutes at a pot temperature of 95° C., until the color of neutralized reaction product became yellow.

The neutralized reaction product was then distilled under a vacuum of below 0.5 torr at a heat temperature of below 200° C. At this point in the process, the distilled mixture contained an alcohol residue having less than 2% of the distilled reaction product's weight.

The distilled reaction product was then diluted with 34 kg of refined ion water having 4.5~5.0 pH. The diluting step was carried out in the sealed vessel which have an outlet operated automatically by a level sensor or a pressure sensor, and nitrogen gas was poured into the vessel in the beginning of dilution in order to prevent the mixture from being exposed to oxygen.

This diluted solution was found to have water content of 50%, and a Gardner color number of 4.8.

To the diluted mixture was added 0.9 kg of 30% aqueous solution of sodium hydroxide and was dissolved for 10 minute at a pot temperature of 50° C. And then, 1.7 kg of 28% aqueous solution of hydrogen peroxide was added and stirred for 2 hours at 85° C.

The bleached solution was found to have pale-colored and transparent alkyl glycosides having water content of 50%, transmittance of 97%, and APHA (degree of color) of 25 by an examination with naked eye and instrumental analysis using a tintometer (Lovibond's PFX 190) and transmittace analyser (Milton Roy's spectronic 20 D). The collected alcohol had APHA of 0.

In this disclosure, there is shown and described only the preferred processes of the invention. But, as aforementioned, it is to be understood that the invention is capable of use in various other combinations and environments and is capable of changes or modification within the scope of the inventive concepts as expressed herein.

What is claimed is:

1. A process of preparing pale-colored and transparent alkyl glycosides comprising the steps of:
   1) admixing glucose with a high fatty alcohol having 8 to 22 carbon atoms;
   2) reacting the mixture in the presence of an acid catalyst at a high temperature and a high vacuum condition until a reaction product's color is between ochre and wormwood and an amount of an unreacted glucose reaches below 3% of a reactants' weight;
   3) neutralizing the reaction product having water content of less than 1000 ppm by means of adding alkali metal oxide powder having a specific surface area of greater than 30 m$^2$/g as a neutralizing agent and stirring until the reaction product's color is yellow and the reaction product pH is between 7.0–8.0;
   4) distilling the neutralized reaction product to remove unreacted residual fatty alcohol at a high temperature and a high vacuum condition until an amount of an unreacted fatty alcohol reaches below 2% of the distilled reaction product's weight;
   5) diluting the distilled reaction product by means of adding refined ion water having pH between 2.0 and 6.0, in a vessel sealed and charged with nitrogen gas;
   6) bleaching the diluted reaction product with a small amount of a bleaching agent.

2. The process according to claim 1, wherein the high fatty alcohol in step 1) is in an amount of 3~5 mole per mole of glucose.

3. The process according to claim 1, wherein the acid catalyst in step 2) is in an amount of 0.002~0.007 mole per mole of glucose.

4. The process according to claim 1, wherein the reaction in step 2) is conducted at a temperature range of 110~125° C.

5. The process according to claim 1, wherein the reaction in step 2) is conducted under a vacuum pressure of 16~20 torr.

6. The process according to claim 1, wherein the reaction in step 2) is conducted for 80~200 minutes.

7. The process according to claim 1, wherein the alkali metal oxide powder of the neutralizing agent in step 3) is magnesium oxide, aluminum oxide, calcium oxide, zinc oxide or their mixture.

8. The process according to claim 1, wherein the neutralizing agent in step 3) is in an amount of from 0.5 mole to 1.0 mole, based on the acid catalyst used, on a molar basis.

9. The process according to claim 1, wherein the stirring process in step 3) is conducted at 85~105° C.

10. The process according to claim 1, wherein the stirring process in step 3) is conducted for 20 minutes to 40 minutes.

11. The process according to claim 1, wherein the distillation process in step 4) is carried out by a thin film evaporator.

12. The process according to claim 1, wherein the diluted reaction product in step 5) is of yellow color having a Gardner number ranging from 4 to 11.

13. The process according to claim 1, wherein the dilution in step 5) is conducted in a concentration of 40~60%.

14. The process according to claim 1, wherein a residue of the bleaching agent in step 6) is decreased from the reaction product by a heat exchanger.

15. The process according to claim 1, wherein the removed residual fatty alcohols are collected and recycled without being refined.

16. A process of preparing pale-colored and transparent alkyl glycosides comprising the steps of:
   1) reacting glucose and a high fatty alcohol of having 8 to 22 carbon atoms in the presence of an acid catalyst until an amount of an unreacted glucose in reaction product reaches less than 3% of a reactants weight;
   2) neutralizing the reaction product by means of adding magnesium oxide powders having a specific surface area of greater than 50 m$^2$/g at a temperature of 85–105° C. for 20–40 minutes until pH of the reaction product is between 7.0–8.0;
   3) distilling the neutralized reaction product until an amount of an unreacted residual fatty alcohol reaches less than 2% of a distilled reaction products weight;
   4) diluting the distilled reaction product; and
   5) bleaching the diluted reaction product with hydrogen peroxide.

17. The process according to claim 16, wherein the acid catalyst in step 1) is para-toluene sulfonic acid (p-TSA).

18. The process according to claim 16, wherein the magnesium oxide in step 2) is in an amount of from 0.5 mole to 1.0 mole, based on the acid catalyst used, on a molar basis.

19. The process according to claim 16, wherein the magnesium oxide in step 2) has a specific surface area of greater than 80 m$^2$/g.

20. The process according to claim 16, wherein the distillation process in step 3) is carried out by a thin film evaporator.

21. The process according to claim 16, wherein the removed residual fatty alcohols are collected and recycled without being refined.

22. A process of preparing pale-colored and transparent alkyl glycosides comprising the steps of:
   1) reacting glucose and a high fatty alcohol of having 8 to 22 carbon atoms in presence of an acid catalyst until an amount of an unreacted glucose in reaction product reaches less than 3% of a reactants weight;
   2) neutralizing the reaction product having water content of less than 1000 ppm by means of adding alkali metal oxide powders selected from the group consisting of magnesium oxide, aluminum oxide, calcium oxide, zinc oxide, and their mixture, having a specific surface area of more than 30 m$^2$/g, until pH of the reaction product is between 7.0–8.0.

23. The process according to claim 22, wherein the alkali metal oxide in step 2) is in an amount of from 0.5 mole to 1.0 mole, based on the acid catalyst used, on a molar basis.

24. The process according to claim 22, wherein the alkali metal oxide in step 2) has a specific surface area of greater than 50 m$^2$/g.

25. The process according to claim 22, wherein the neutralization in step 2) is carried out by stirring for 20–60 minutes at a temperature of 85–105° C.

26. The process according to claim 22, wherein the reaction product in step 2) has water content of less than 500 ppm.

27. The process according to claim 22, wherein the removed residual fatty alcohols are collected and recycled without being refined.

28. A process of preparing pale-colored and transparent alkyl glycosides comprising the steps of:
1) reacting a glucose and a high fatty alcohol in presence of an acid catalyst;
2) neutralizing the reaction product by means of adding neutralization agent until the reaction product pH reaches 7.0~8.0;
3) distilling the neutralized reaction product; then
4) diluting the distilled reaction product by means of adding refined ion water having pH range of 2.0~6.0, in a vessel sealed and charged with nitrogen gas.

29. The process according to claim 28, wherein the refined ion water has pH range of 3.0~5.0.

30. The process according to claim 28, wherein the vessel in step 4) has an outlet operated automatically by a level sensor or a pressure sensor.

31. The process according to claim 28, wherein the removed residual fatty alcohols are collected and recycled without being refined.

32. A process of preparing pale-colored and transparent alkyl glycosides comprising the steps of:
1) admixing glucose and a high fatty alcohol having 8 to 22 carbon atoms;
2) reacting the mixture in presence of an acid catalyst until a reaction product's color is between ochre and wormwood and an amount of an unreacted glucose reaches less than 3% of reactants' weight;
3) neutralizing the reaction product by means of adding magnesium oxide powders and stirring until the reaction product's color is yellow and the reaction product pH is between 7.0–8.0;
4) distilling the neutralized reaction product until an amount of an unreacted residual fatty alcohol reaches less than 2% of the distilled reaction product's weight;
5) diluting the distilled reaction product; then
6) bleaching the diluted reaction product with hydrogen peroxide.

33. The process according to claim 32, wherein the neutralizing process is carried out by stirring for 20~60 minutes at 85–105° C.

34. The process according to claim 32, wherein the removed residual fatty alcohols are collected and recycled without being refined.

* * * * *